United States Patent [19]

Johansson et al.

[11] Patent Number: 4,906,237
[45] Date of Patent: Mar. 6, 1990

[54] METHOD OF FORMING AN IMPROVED HYDROPHILIC COATING ON A POLYMER SURFACE

[75] Inventors: Eva G. Johansson, Göteborg; Jan M. R. Utas-Sjöberg, Mölndal, both of Sweden

[73] Assignee: Astra Meditec AB, Molndal, Sweden

[21] Appl. No.: 232,139

[22] Filed: Aug. 24, 1988

Related U.S. Application Data

[63] Continuation of Ser. No. 907,598, Sep. 12, 1986, abandoned.

[30] Foreign Application Priority Data

Sep. 13, 1985 [SE] Sweden ................................ 8504501

[51] Int. Cl.$^4$ .......................................... A61M 5/325
[52] U.S. Cl. ................................................... 604/265
[58] Field of Search ................... 604/265, 266; 623/11; 523/105; 424/80

[56] References Cited

U.S. PATENT DOCUMENTS

| | | | |
|---|---|---|---|
| 2,872,433 | 2/1959 | Glickman | 424/80 |
| 3,886,947 | 6/1975 | Sawyer | 604/266 |
| 3,895,169 | 7/1975 | Wichterle | 428/420 |
| 3,975,350 | 8/1976 | Hudgin et al. | 128/334 R |
| 4,053,696 | 10/1977 | Herrle et al. | 424/80 |
| 4,094,967 | 6/1978 | Gilbert | 424/80 |
| 4,100,309 | 7/1978 | Micklus | 428/423.3 |
| 4,119,094 | 10/1978 | Micklus et al. | 604/349 |
| 4,143,423 | 3/1979 | Sternlieb | 604/265 |
| 4,318,947 | 3/1982 | Joung | 604/265 |
| 4,373,009 | 2/1983 | Winn | 604/280 |
| 4,515,593 | 5/1985 | Norton | 604/265 |
| 4,526,579 | 7/1985 | Ainpour | 604/266 |
| 4,585,666 | 4/1986 | Lambert | 604/280 |
| 4,589,873 | 5/1986 | Schwartz et al. | 604/265 |
| 4,666,437 | 5/1987 | Lambert | 604/265 |
| 4,677,143 | 6/1987 | Laurin et al. | 604/265 |

FOREIGN PATENT DOCUMENTS

| | | |
|---|---|---|
| 093093 | of 0000 | European Pat. Off. . |
| 159034 | of 0000 | European Pat. Off. . |
| 168917 | of 0000 | European Pat. Off. . |

OTHER PUBLICATIONS

March, Jerry, *Advanced Organc Chemistry*, 1977, 2nd Edition, pp. 170-179.

*Primary Examiner*—C. Fred Rosenbaum
*Assistant Examiner*—Sharon Rose
*Attorney, Agent, or Firm*—White & Case

[57] ABSTRACT

A method of forming an improved hydrophilic coating by applying on a non-reactive hydrophilic polymer surface layer an osmolality-increasing compound to produce a more stable hydrophilic surface and to produce a more slippery surface in wet condition. The polymer surface layer is treated with a solution having above 2% (weight/volume) of an osmolality increasing compound and then the solvent of the solution is evaporated. Osmolality increasing compounds are nontoxic organic or unorganic salts other than trihalogenids, mono- or di- saccharides or sugar alcohols. Preferred compounds are glucose, sorbitol, sodium chloride, sodium citrate, sodium bensoate, calcium chloride, potassium chloride, potassium iodide, potassium nitrate. The solution of the osmolality increasing compound contains preferably a polymer. Medical articles treated with the solution of osmolality increasing compounds according to the method above also relate to the invention.

20 Claims, No Drawings

METHOD OF FORMING AN IMPROVED HYDROPHILIC COATING ON A POLYMER SURFACE

SPECIFICATION

This is a continuation application based on Ser. No. 907,598, filed on Sept. 12, 1986, now abandoned.

BACKGROUND OF THE INVENTION

This invention relates to a method of coating a hydrophilic polymer surface layer with an osmolality increasing compound to produce a more stable hydrophilic surface as well as medical articles being coated with said improved hydrophilic coatings.

Hydrophilic coatings have a much lower coefficient of friction when wet than when dry. Thus, the formation of hydrophilic coatings on substrates has many applications and, in particular, is desirable in many biomedical applications. For example, biomedical devices such as wound drains, catheters, surgical tools and other medical instruments intended for insertion in the body cavities are advantageously coated with a hydrophilic substance, because the instrument gives a good hand grip in dry condition while simultaneously becoming very slippery when it comes in contact with water-based liquids. Thus, the device can be inserted easily without causing trouble to the patient. Further, an article having a hydrophilic surface coating is desirable to minimize thrombosis, crystal formation, tissue trauma, tissue adhesion to medical instruments, and foreign body reactions. In prior art methods, surfaces have been rendered hydrophilic by such methods as high energy radiation in situ polymerization processes, by grafting, by forming an interpolymer network or by direct chemical bonding, for instance, by isocyanates or silanes. Such hydrophilic polymer surfaces for medical use are described for instance in G.B Pat. No. 1,600,963, U.S. Pat. No. 4,373,009, U.S. Pat. No. 4,459,317, WO 83/03977 and European Patent Application 83850090.8. Extensive studies indicate, however, that the hydrophilic coating can dry out, thus rendering the article insufficiently hydrophilic.

DESCRIPTION OF THE INVENTION

The object of the present invention is to prepare an improved hydrophilic coating on an already hydrophilic polymer surface layer on a substrate. This object of the invention has surprisingly been achieved by applying a solution of an osmolality increasing compound to a non-reactive hydrophilic polymer surface layer and then evaporating the solvent of the solution.

While experimenting with hydrophilic polymer coatings on various substrates, the applicant found that when an article coated with a hydrophilic polymer surface layer is dipped in water it will be well wetted. There is, however, a great risk that the polymer surface will lose the water when it comes in contact with a mucous membrane or the like. This occurs because of the difference in the osmotic potential between the hydrophilic surface and the mucous membrane. The mucous membrane has a higher osmotic potential, that is a higher salt concentration than the hydrophilic surface, which causes the water to go from the hydrophilic surface layer to the mucous membrane so that the difference in the salt concentration will be counter-balanced.

According to the invention, it has surprisingly been found possible to further reduce the low friction of the hydrophilic surface and to enhance the osmolality of the hydrophilic surface simultaneously by applying a coating of an osmolality increasing compound to the hydrophilic polymer surface layer. Different types of osmolality increasing compounds can be used, such as inorganic or organic salts, mono- or disaccharides, or sugar alcohols. Examples of such osmolality increasing compounds are glucose, sorbitol, sodium chloride, sodium citrate, sodium benzoate, calcium chloride, potassium chloride, potassium iodide, potassium nitrate. These osmolality increasing compounds must be non-toxic. The process has found to be especially useful for sodium chloride. The osmolality increasing compound may also be mixed with a polymer and dissolved in water or a lower alcohol, preferably in water to a suitable viscosity. Said solution is applied to the hydrophilic polymer surface layer by dipping, spraying or the like and then the solvent is evaporated by air drying or by drying at elevated temperature. The added polymer should be well compatible with the polymer in the hydrophilic polymer surface layer, and should preferably be the same polymer. The polymer is not a necessary additive to the solution but it enhances the viscosity and thus the reception of the osmolality increasing compound can be controlled. Further, the polymer possesses a lubricating property and a controlled release effect.

The process according to the invention can be used for coating many different types of well-known hydrophilic polymer surfaces, wherein the hydrophilic polymer layer is selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The preferred hydrophilic polymer is polyvinylpyrrolidone. The hydrophilic polymer layer must be made non-reactive, for instance by curing.

The substrates may be any polymer material, which are well-known to use and to which the said hydrophilic polymers adhere, such as polyurethanes, latex rubbers, other rubbers, polyvinylchloride, other vinyl polymers, polyesters and polyacrylates.

The hydrophilic surface contains an appreciable amount of partly freely movable polymer chains. Because of this, some coatings can bind a substantial amount of elemental iodine, which is for example the case with free polyvinylpyrrolidone (PVP) and iodine when a hydrophilic surface coated with polyvinylpyrrolidone is treated with a $KI/I_2$ solution. PVP-coated catheters treated with $KI/I_2$ solution have a less slippery surface than corresponding untreated surface, and such $KI_3$-treated catheters dry more quickly.

EXAMPLE

A trimerized hexathylene diisocyanante of biuret type (named Desmodur L 2291; Bayer AG) was dissolved in methylene chloride to a concentration of 6% (weight/volume). A urinary PVC catheter was dipped in this solution for 30 seconds. The catheter was then dried at 70° C. for 60 seconds, whereupon it was dipped for 5 seconds in a solution containing 33 g polyvinylpyrrolidone (K25; mean molecular weight 25,000) per 100 ml methylene chloride. This solution also contained 0.33 g triethylene diamine (DABCO®) per 100 ml solution. The catheter was then allowed to dry at ambient temperature for 60 seconds, then cured for 40 minutes at 70° C., cooled to ambient temperature and was then rinsed in water. Such a catheter was dipped in a solution containing 20% (weight/volume) sodium chloride and 5% polyvinylpyrrolidone (PVP) (weight/volume) dissolved in water for 1 hour at 20° C. The catheter was then allowed to dry at 70° C. for eight hours. The catheter has a very slippery and adherent surface when wet.

EXPERIMENTAL TEST

A number of catheters prepared according to the example were dipped in different solutions comprising osmolality increasing compounds for 10 minutes and were then placed in water during 30 seconds at 23° C. and a relative humidity of 49% and then dried at room temperature. The slipperiness was noted 1 min., 2 min. etc. after drying had already begun. The value of slipperiness was noted in a relative scale, wherein 8 means a very slippery surface and 0 means a dry surface.

This experiment was repeated with a number of corresponding PVP-coated catheters but without the coating of osmolality increasing compound.

TABLE 1

| PVP-coated catheter treated with following solutions | Slipperiness after Drying | | | | |
|---|---|---|---|---|---|
| | 0 min | 1 | 2 | 3 | 4 |
| Untreated | 8 | 7 | 5 | 2 | 1 |
| 20% NaCl + 5% PVP | 8 | 8 | 8 | 8 | 7 |
| 15% KCl + 5% PVP | 8 | 8 | 7 | 7 | 6 |
| 15% Na Citrate + 1% Keltrol ® | 8 | 8 | 8 | 8 | 8 |
| 15% KI | 8 | 8 | 7 | 4 | 2 |
| 15% Glucose + 5% PVP | 8 | 8 | 8 | 7 | 6 |
| 30% Sorbitol + 1% Keltrol ® | 8 | 8 | 8 | 7 | 7 |

Keltrol ® is a xanthan gum; Kelco Co.

Table 1 shows that the catheters having a coating of a non-toxic, osmolality increasing compound retain their slipperiness for a longer time than the corresponding untreated surfaces. In other words, the coated catheters dry more slowly. The osmolality increasing compounds prevent the underlying hydrophilic polymer surface from desiccating.

Thus, catheters applied with an osmolality increasing compound such as sodium chloride according to the invention dry more slowly than corresponding untreated catheters. The sodium chloride treated catheter keeps its slipperiness for a much longer time period, which is very desirable.

Medical tests in urethrea applications show that the catheters applied with a coating of osmolality increasing compounds such as sodium chloride are superior both on insertion and on removal of the catheter.

We claim:

1. A method of forming an improved hydrophilic coating on a substrate, comprising:
   (a) applying a non-reactive hydrophilic polymer layer to the substrate;
   (b) applying to the non-reactive hydrophilic polymer layer a solution comprising a solvent and at least 2% (weight per volume) of an osmolality-increasing compound selected from the group consisting of mono and disaccharides, sugar alcohols, and non-toxic organic and inorganic salts, with the proviso that the osmolality-increasing compound is not a trihalogenide; and
   (c) evaporating the solvent.

2. A method according to claim 1 wherein the osmolality-increasing compounds is selected from the group consisting of glucose, sorbitol, sodium chloride, sodium citrate, sodium benzoate, calcium chloride, potassium chloride, potassium iodide and potassium nitrate.

3. A method according to claim 1, wherein the osmolality-increasing compound is selected from the group consisting of glucose, sodium chloride, sodium citrate, sodium benzoate, calcium chloride, potassium chloride, potassium iodide and potassium nitrate.

4. A method according to claim 1, wherein the solution further comprises a polymer.

5. A method according to claim 1, wherein the solution contains about 4% to about 40% (weight to volume) of sodium chloride.

6. A method according to claim 1, further comprising the step of curing the polymer layer prior to treatment with the osmolality-increasing agent.

7. A method according to claim 1, wherein the polymer layer comprises a polymer selected from the group consisting of polyethuleneoxide, polyvinylpyrrolidone, polyvinyl compounds, polysaccharides, polyurethanes, polyacrylates and copolymers thereof.

8. A method according to claim 1, wherein the polymer layer comprises polyvinylpryyolidone, and the solution comprises 20% (weight/volume) sodium chloride.

9. A method according to claim 4, wherein the polymer contained in the solution is the same polymer as is used in the non-reactive hydrophilic polymer surface layer.

10. A method according to claim 1, wherein the osmolality-increasing compound is selected from the group consisting of glucose and sorbitol.

11. A method according to claim 10, wherein the osmolality-increasing compound is selected from the group consisting of glucose and sorbitol.

12. A method according to claim 1, wherein the osmolality-increasing compound is selected from the group consisting of sodium chloride, potassium chloride, calcium chloride, potassium iodide and potassium nitrate.

13. A medical article according to claim 1, wherein the osmolality-increasing compound is selected from the group consisting of sodium chloride, potassium chloride, calcium chloride, potassium iodide and potassium nitrate.

14. A medical article having a very low coefficient of friction when wetted with a water-based liquid comprising:
   (a) substrate,
   (b) a non-reactive hydrophilic polymer layer disposed on the surface of said substrate; and
   (c) an evaporated hydrophilic coating disposed on the polymer layer, said evaporated hydrophilic coating comprising an osmolality-increasing compound selected from the group consisting of non-toxic organic and inorganic salts, mono- and disaccharides, and sugar alcohols, with the proviso that the osmolality-increasing agent is not a trihalogenide.

15. A medical article according to claim 14, wherein the osmolality-increasing compound is selected from the group consisting of glucose, sorbitol, sodium chloride, sodium citrate, sodium benzoate, calcium chloride, potassium chloride, potassium iodide, and potassium nitrate.

16. A medical article according to claim 14, wherein osmolality-increasing compound is selected from the group consisting of glucose, sodium chloride, sodium citrate, sodium benzoate, calcium chloride, potassium chloride, potassium iodide, and potassium nitrate.

17. A medical article according to claim 14 which is catheter.

18. A medical article according to claim 17 which is a urinary catheter.

19. A medical article according to claim 14, wherein the osmolality-increasing compound is selected from the group consisting of mono- and disaccharides and sugar alcohols.

20. A medical article according to claim 19, wherein the osmolality-increasing compound is selected from the group consisting of glucose and sorbitol.

* * * * *